United States Patent [19]

Nethercutt et al.

[11] 4,035,911
[45] July 19, 1977

[54] SYRINGE DESTROYER WITH NEEDLE DISPOSING CANNISTER

[76] Inventors: Henry W. Nethercutt, 82 Sycamore St.; Edward J. Lambiotte, 3022 Wallace Circle, Huntington, both of W. Va. 25705

[21] Appl. No.: 716,796

[22] Filed: Aug. 23, 1976

[51] Int. Cl.² .................. B26B 13/22; B26D 3/16
[52] U.S. Cl. .............................. 30/131; 30/242; 83/167
[58] Field of Search ............ 30/124, 125, 131, 134, 30/241, 242; 83/167, 580

[56] References Cited

U.S. PATENT DOCUMENTS

| 3,404,593 | 10/1968 | Arcarese | 83/167 |
| 3,683,733 | 8/1972 | Johan | 83/580 X |
| 3,736,824 | 6/1973 | Dunnican | 83/167 |
| 3,785,233 | 1/1974 | Robinson | 83/167 |
| 3,851,555 | 12/1974 | Eldridge | 83/167 |
| 3,914,865 | 10/1975 | Oakes | 30/131 |

*Primary Examiner*—Al Lawrence Smith
*Assistant Examiner*—J. C. Peters
*Attorney, Agent, or Firm*—Strauch, Nolan, Neale, Nies & Kurz

[57] ABSTRACT

A compact, hand operated syringe destroyer for severing the needle and its hub from the barrel of an associated syringe and a cannister for collecting a quantity of such severed needles. When filled, the cannister is easily closed and discarded.

9 Claims, 6 Drawing Figures

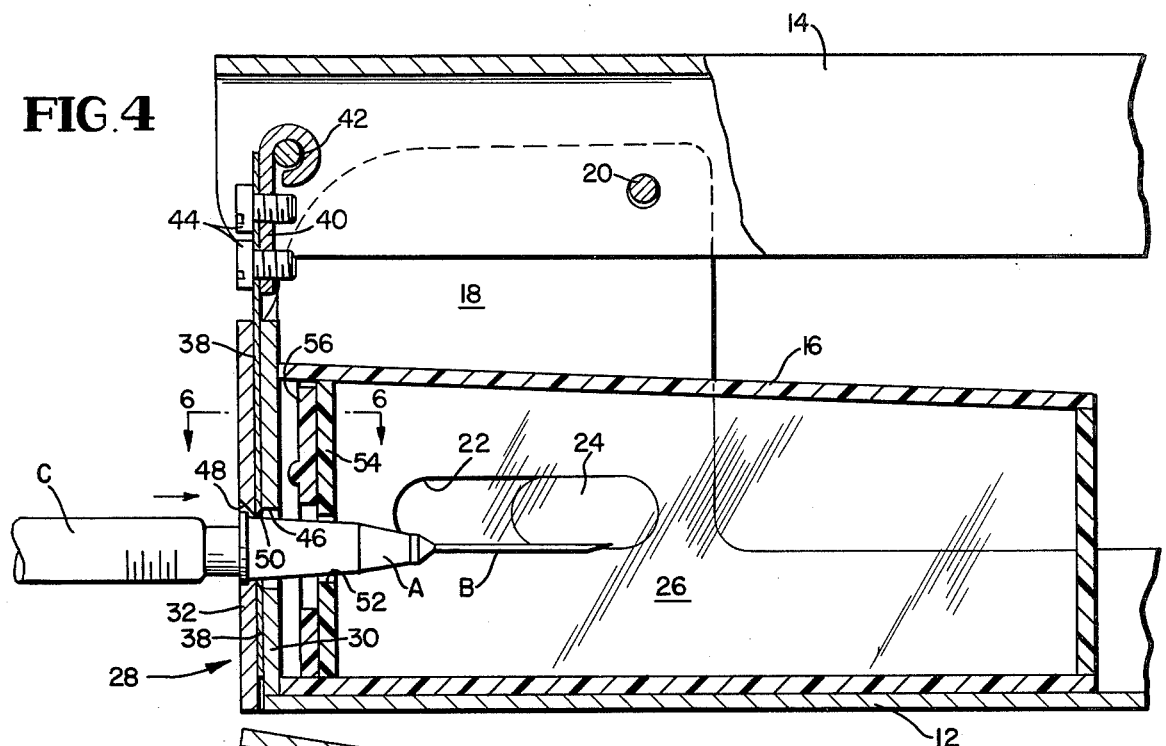
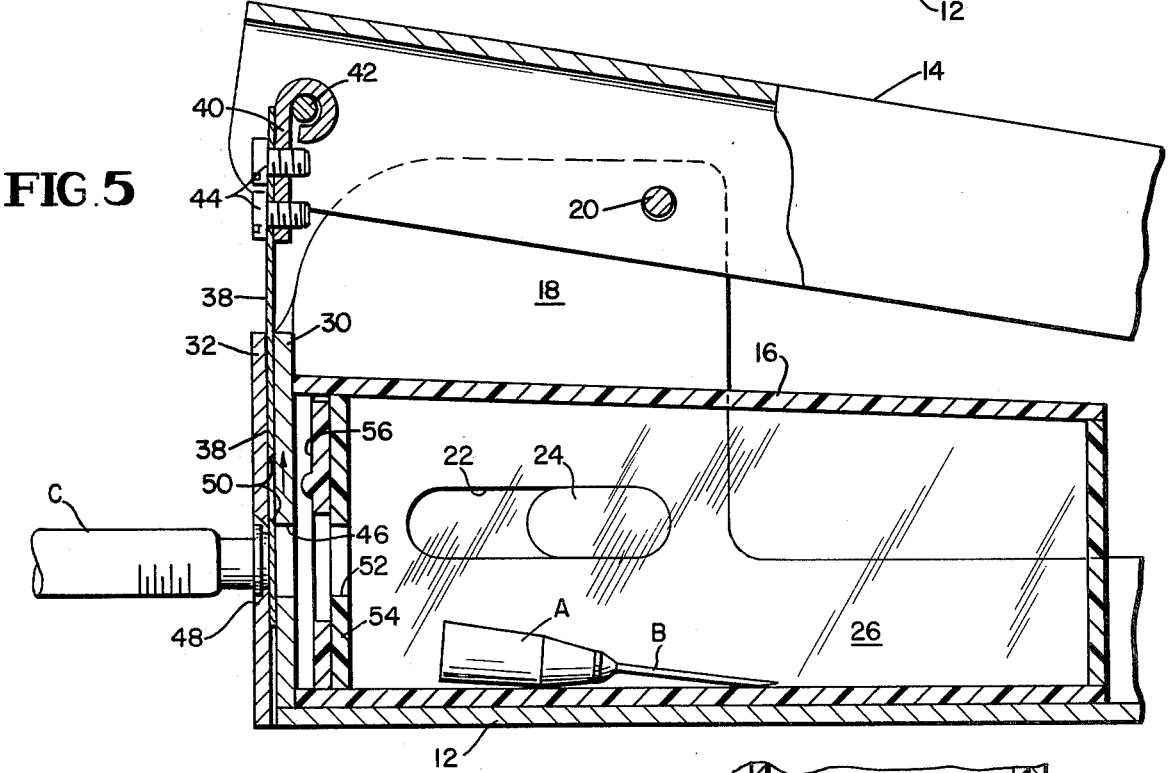
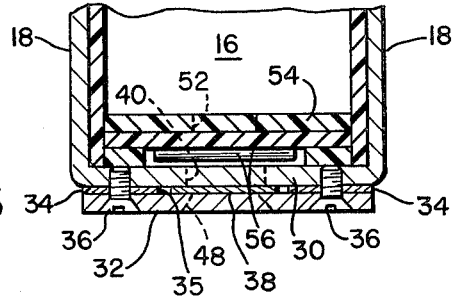

SYRINGE DESTROYER WITH NEEDLE DISPOSING CANNISTER

BACKGROUND OF THE INVENTION

The invention concerns a device for destroying hypodermic syringes and needles so that they cannot be re-used and includes a disposable cannister for collecting needles and hubs severed from their syringes.

Hypodermic syringes of the type now in widespread use in hospitals are generally intended for a single use. After such use, however, they cannot be discarded because of the danger of unauthorized or illegal re-use and because they cannot be handled without a substantial risk of injury or infection.

In recognition of this problem, the prior art includes a number of proposals of varying complexity and cost for destroying such syringes and for permitting safe disposal of the syringe needles.

Representative of the more complex and expensive devices of the prior art is the electro-mechanical device disclosed in U.S. Pat. No. 3,469,750.

The expanse of such a device renders it unsuitable for the intended purpose, particularly since syringes are used at a number of locations in hospitals, and experience has shown that unless a disposal device is readily at hand at each location, the syringes and needle assemblies will be discarded without prior destruction.

Other less complicated manually operable devices for destroying syringes are disclosed in U.S. Pat. Nos. 3,404,593, 3,444,620, 3,585,835, 3,736,824 and 3,914,865.

None of these devices have provided a satisfactory solution to the problem, either because they are relatively difficult to operate, require one on more operations to complete destruction of a syringe, or do not provide for safe disposition of the severed needles.

Additionally, a disposable device, such as that disclosed in U.S. Pat. No. 3,914,865, is excessively expensive and, in view of the frequent use of the device, a substantial inventory of such devices must be maintained to assure their uninterrupted use. Further, in such a device, a two-step operation is required in order to sever the needle and the hub.

The present invention provides a hand-operated mechanism effective to separate both needle and hub from the syringe barrel in a one-step operation. The destroyed syringe, which is neither dangerous nor reusable, is then disposed of separately. The severed needles and hubs are deposited in a disposable cannister which is of a size and configuration to hold a quantity of needles and hubs. Once filled, it is removed from the severing device and sealed and thereafter discarded and replaced by a fresh empty cannister. Thus, the unit of the present invention may be made durable and reliable without the compromise dictated by cost requirements in a fully disposable device.

SUMMARY OF THE INVENTION

Therefore, it is a principal object of the invention to provide a syringe destroying device operable in one step fashion to sever a needle and its associated hub from the syringe barrel.

It is another object of the invention to provide a syringe destroying device having a removable, discardable cannister component for collecting needles and hubs as they are severed from their associated syringe barrels.

It is a further object of the invention to provide a syringe destroying device which is hand operable and compact in size so as to be easily carried about on one's person.

It is yet another object of the invention to provide a syringe destroying device wherein a blade for severing the needle and hub from the syringe may be easily replaced when worn or dulled from use.

It is yet a further object of the invention to provide a syringe destroying device including a port through which the hub and needle of a syringe are inserted, the port having a bevelled profile and operable in unison with an interiorally mounted, reciprocable shearing blade so that the hub and needle are neatly and easily sliced from their associated syringe barrel rather than being sheared or even broken off as is the case with many of the prior art devices.

Further novel features and other objects of this invention will become apparent from the following detailed description, discussion and the appended claims taken in conjunction with the accompanying drawings.

BRIEF DESCRIPTION OF DRAWINGS

FIG. 4 is a section view taken along lines 4—4 of FIG. 3, drawn to an enlarged scale and showing disposition of parts as a needle and its associated hub are about to be severed from a syringe barrel;

FIG. 5 is a section view similar to FIG. 4 showing disposition of parts just after a needle and its associated hub have been severed from a syringe barrel; and FIG. 6 is a detail section view taken along lines 6—6 of FIG. 4.

DESCRIPTION OF THE PREFERRED EMBODIMENT

Figure 1:
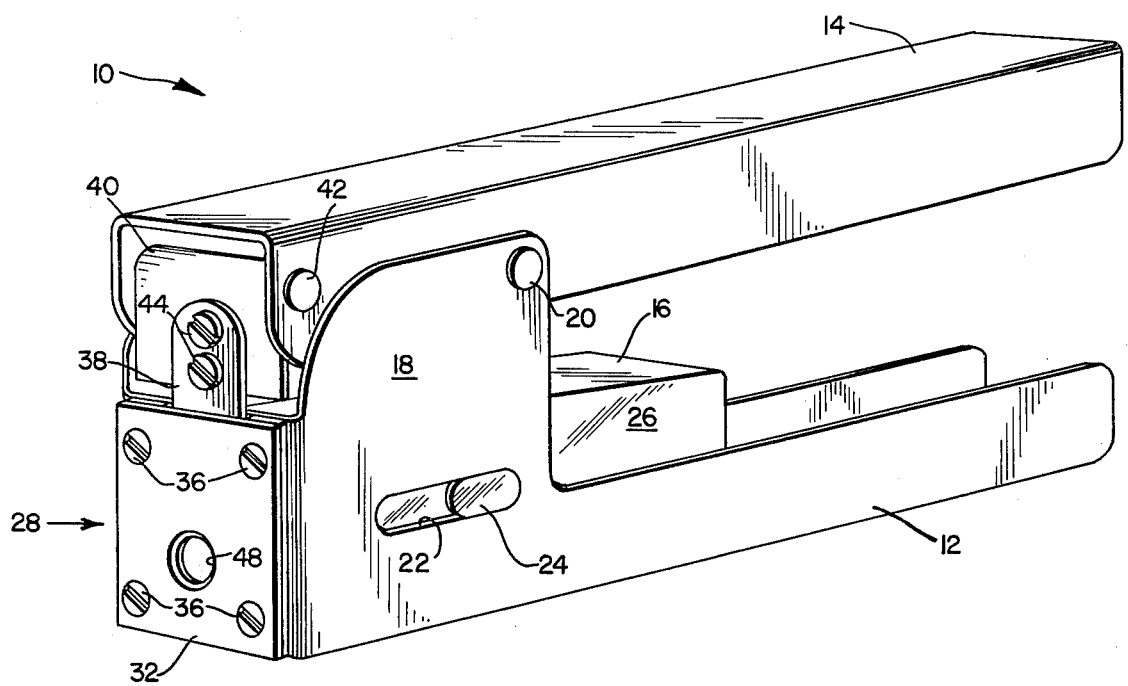
FIG. 1 is a perspective view of the entire device in assembly.
Figure 3:
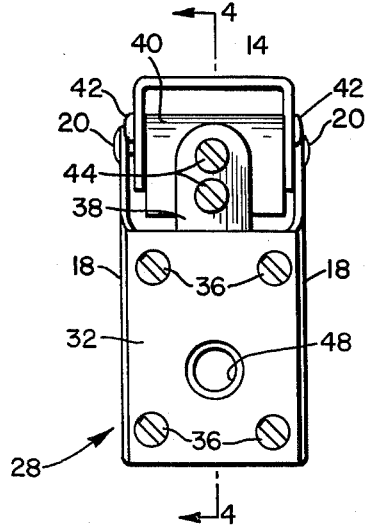
FIG. 3 is an elevation front view of the invention as shown in FIG. 1.
Figure 2:
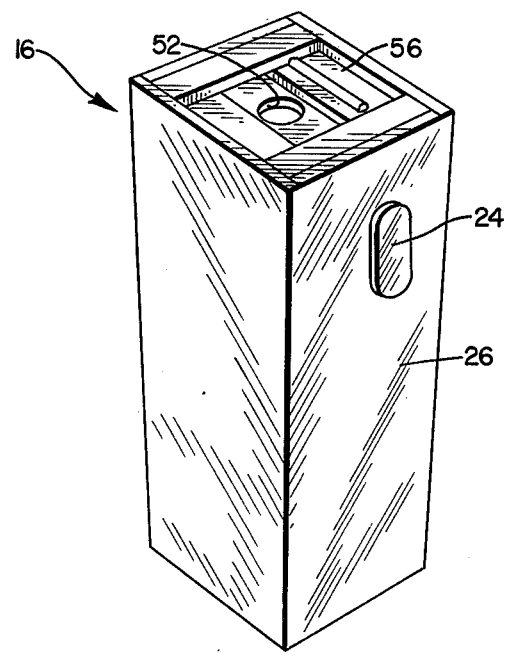
FIG. 2 is a perspective view of the disposable cannister.

The basic, major components of the preferred embodiment of the syringe destroyer 10 include a base member 12, an upper, pivotal handle 14 and a disposable severed needle and hub collection cannister 16. A pair of forward, opposed side walls 18 are formed integrally with base member 12 and include a pivot pin 20 for mounting handle 14 and opposed slots 22 cooperating with lugs 24 formed in opposed side walls 26 of cannister 16 for retaining canister 16 in snap-fit assembly with base member 12. Slots 22 may be elongated as shown to provide convenient viewports whereby the condition of cannister 16 (which may be molded of clear plastics material) may be continually monitored to determine when it is filled with severed needles and hubs and is thus ready for disposal and replacement with a fresh cannister.

The severing component 28 of the assembly includes a front end wall assembly formed of a pair of plates 30, 32 spaced apart by spacers 34 (FIG. 6). The rearward plate 30 may be formed integrally with side walls 18 of base 12, as clearly shown in FIG. 6, and the forward plate 32 is retained therein by mounting screws 36 which extend through spacers 34. Thus, spacers 34 define a vertical slot 35 between plates 30, 32 within which severing blade 38 is mounted for vertical, reciprocal severing movement. A depending blade mounting member 40 is pivotally secured to the front end of handle 14 by a pin 42. Blade 38 is attached to member 40 by a pair of mounting screws 44 so that it may be replaced by a fresh blade when worn or dulled from use.

As is illustrated in FIG. 4, walls 30 and 32 include open ports 46 and 48, respectively, which may be aligned with each other and with a severing port 50 formed through blade 38 and with an insertion port 52 formed through end 54 of cannister 16. With the several ports so aligned, the hub A and needle B of a disposable syringe assembly including a syringe barrel C are inserted as shown in FIG. 4 with hub A and needle B inside cannister 16. Handle 14 and base 12 are then grasped and brought together in order to sever hub A and needle B from syringe barrel C, as shown in FIG. 5. This occurs by reason of the lifting action on blade 38 caused by lowering of handle 14, as indicated by the arrows in FIG. 5, whereby severing port 50 cuts hub A off of syringe barrel C.

As can be seen in both FIGS. 4 and 5, open port 48 of front wall 32 is bevelled rearwardly to a cutting edge and severing port 50 is bevelled forwardly towards open port 48 so that, as blade 38 is brought upwardly, hub A with needle B is neatly and effortlessly sliced from syringe barrel C.

Once cannister 16 is filled with severed needles and hubs, it maybe removed from base 12 and sealed closed by sliding cover 56 over insertion port 52. Cannister 16 may then be discarded and replaced by a fresh cannister.

In this preferred embodiment, the entire assembly, except for cannister 16, may be made of surgical steel so that the instrument may be fully autoclaved. In addition, the unit is strong enough to withstand accidental shock and abuse. Thus, it is a permanent instrument, designed for years of use. In this regard, it is to be noted further that in addition to blade 38, front wall 32 with its bevelled, cutting port 48 may also be removed and replaced if it becomes dulled from use by means of mounting screws 36.

The invention may be embodied in other specific forms without departing from the spirit of essential characteristics thereof. The present embodiment is therefore to be considered in all respects as illustrative and not restrictive, the scope of the invention being indicated by the appended claims rather than by the foregoing description; and all changes which come within the meaning and range of equivalency of the claims are therefore intended to be embraced therein.

We claim:

1. A hand operated device for severing a hypodermic needle and its associated hub from a syringe barrel comprising an elongate base member having opposed, upstanding side walls; a front end wall assembly joining said side walls; means defining open port means in said front end wall assembly through which the needle and associated hub of a syringe assembly are inserted for severing; reciprocating blade means for severing a needle and its hub from a syringe assembly; means mounting said blade means in said front end wall assembly for reciprocating movement therein in response to hand manipulation; means defining a severing port in said blade means, cooperating with said front end open port means whereby, in one position, said ports are alligned for insertion of the needle and hub of a syringe assembly therethrough and, upon hand manipulation of said blade means to another position, the hub and needle are severed from a syringe assembly; and removable cannister means disposed between said side walls, and having insertion port means aligned with said front end wall assembly open port means for receiving a needle and its hub during severance from a syringe assembly, said cannister means retaining said needle and hub after severance from its syringe assembly.

2. The hand operated needle and hub severing device as claimed in claim 1 wherein said vertical front end wall assembly comprises a pair of plates, spaced apart to define a slot therebetween within which said blade means are disposed for reciprocal movement.

3. The hand operated needle and hub severing device as claimed in claim 2 wherein said open port means comprise a pair of aligned ports formed in the respective said pair of plates.

4. The hand operated needle and hub severing device as claimed in claim 3 wherein the said aligned port in one of said pair of plates is formed with a bevelled cutting edge arranged to cooperate with a mating, bevelled cutting edge formed in said blade means severing port whereupon, in operation, said bevelled cutting edges neatly slice a hub and needle from their associated syringe.

5. The hand operated needle and hub severing device as claimed in claim 1 wherein said means for mounting said blade means include a graspable handle, pivotally mounted between the upper terminal ends of said base member side walls, and blade mounting means pivotally mounted on and depending from the forward end of said graspable handle means, above said base member front end wall assembly.

6. The hand operated needle and hub severing device as claimed in claim 5 wherein said pivotally mounted, depending blade mounting means further comprise means detachably securing said blade means thereto.

7. The hand operated needle and hub severing device as claimed in claim 1 wherein said cannister means further comprise a cover for sealing closed said cannister insertion port after said cannister means has been filled with severed needles and hubs and removed from said base member for disposal.

8. The hand operated needle and hub severing device as claimed in claim 1 wherein said cannister means further comprise a pair of projecting lugs formed on opposed side walls thereof, said base member pair of side walls further comprising reception slots formed therein for receiving said lugs in snap-fit assembly therein whereby said cannister means are firmly mounted within said base member with said cannister means insertion port aligned with said open port means.

9. The hand operated needle and hub severing device as claimed in claim 8 wherein each of said lug reception slots is formed with a sufficient length dimension as as to form a view port through the associated wall, at least said cannister means opposed side walls being made of transparent material whereby said cannister means may be continually visually internally inspected to determine when it is filled with severed needles and hubs.

* * * * *